United States Patent
Robidoux et al.

(10) Patent No.: US 6,201,118 B1
(45) Date of Patent: Mar. 13, 2001

(54) PROCESS FOR FORMING AN N-ACYLATED, N,N-CONTAINING BICYCLIC RING FROM PIPERAZIC ACID OR AN ESTER THEREOF ESPECIALLY USEFUL AS AN INTERMEDIATE IN THE MANUFACTURE OF A CASPASE INHIBITOR

(75) Inventors: Andrea L. C. Robidoux, Andover; Jeffrey Douglas Wilson, Boxford, both of MA (US); Petra Dietrich, Oxfordshire (GB); Neil Storer, Oxfordshire (GB); Stefania Leonardi, Oxfordshire (GB)

(73) Assignee: Vertex Pharmaceuticals Inc., Cambridge, MA (US)

( * ) Notice: Subject to any disclaimer, the term of this patent is extended or adjusted under 35 U.S.C. 154(b) by 0 days.

(21) Appl. No.: 09/136,339

(22) Filed: Aug. 19, 1998

(51) Int. Cl.$^7$ .................................................. C07D 487/04
(52) U.S. Cl. ............................................... 540/500
(58) Field of Search ............................................... 540/500

(56) References Cited

U.S. PATENT DOCUMENTS 4,940,718 * 7/1990 Barnett .................................. 514/370
5,716,929   2/1998 Bemis et al. .

FOREIGN PATENT DOCUMENTS 98 05242    4/1998  (FR) .
98 05243    4/1998  (FR) .
WO97/22619  6/1997  (WO) .

OTHER PUBLICATIONS

Weygand Preparative Organic Chemistry pp 464–472, 1972.*

M.R. Attwood et al., "The Design and Synthesis of the Angiotensin Converting Enzyme Inhibitor Cilazipril and Related Bicyclic Compounds", 1986, 1011–1019, J. Chem Soc Perkin Trans.

* cited by examiner

*Primary Examiner*—Robert Gerstl
(74) *Attorney, Agent, or Firm*—Andrew S. Marks; Ian Robert Silverman

(57) ABSTRACT

The invention relates to a process for simultaneously N(2)-acylating piperazic acid or an ester thereof and forming a bicyclic ring structure. The invention also relates to the use of that process step in a method of synthesizing a bicyclic compound useful as an intermediate for the production of an inhibitor of a caspase, particularly an inhibitor of interleukin-1β converting enzyme ("ICE").

11 Claims, No Drawings

PROCESS FOR FORMING AN N-ACYLATED, N,N-CONTAINING BICYCLIC RING FROM PIPERAZIC ACID OR AN ESTER THEREOF ESPECIALLY USEFUL AS AN INTERMEDIATE IN THE MANUFACTURE OF A CASPASE INHIBITOR

TECHNICAL FIELD OF THE INVENTION

The invention relates to a process for simultaneously N(2)-acylating piperazic acid or an ester thereof and forming a bicyclic ring structure. The invention also relates to the use of that process step in a method of synthesizing a bicyclic compound useful as an intermediate for the production of an inhibitor of a caspase, particularly an inhibitor of interleukin-1β converting enzyme ("ICE").

BACKGROUND OF THE INVENTION

Compounds containing a bicyclic aza-containing ring systems have been prepared as conformationally restricted dipeptide surrogates for a variety of medically important compounds. In particular, such ring systems are present in angiotensin converting enzyme (ACE) inhibitors, such as Cilazapril®, and in caspase inhibitors, such as inhibitors of interleukin-1 converting enzyme (ICE).

Current methods for synthesizing compounds containing these byciclic aza-containing ring systems have many disadvantages. The typical methods of forming this ring system have been described [EP 94,095, WO 95/35308, WO 97/22619, U.S. Pat. Nos. 5,656,627, 5,716,929 and 5,756,486 and J. P. Kim, et al., *Tetrahedron Letters*, 38, pp. 4935–4938 (1997)].

These methods involve coupling an appropriately protected amino acid with the appropriately N(1)-protected piperazic acid or ester. After deprotection, the bicyclic system is then formed via an acid chloride coupling at the N(1) position.

The main disadvantages to such methods are the use of expensive reagents and the number of steps required for protection and deprotection making the overall process extremely time consuming. Moreover, these methods are often useful for research purposes but are not amenable to large scale production.

In order to be more commercially feasible, it would be desirable to produce compounds containing a byciclic aza-containing ring system in an easier, less expensive manner than has been previously described.

SUMMARY OF THE INVENTION

Applicant has solved this problem by providing a new method of simultaneously N(2)-acylating an N(1)-protected piperazic acid or an ester thereof and creating a bicyclic ring structure comprising that acylated piperazic acid or ester.

This method involves the formation of the desired bicyclic system in two, simple steps. This method also utilizes inexpensive reagents, in that no selective protection/deprotection is necessary and is quite amenable to large scale production. Moreover, this method produces very little contaminating by-products. And this method preserves chirality between the N(1)-protected piperazic acid or an ester thereof and the resulting byciclic aza-containing ring system.

This method is particularly useful for producing an intermediate that may be subsequently converted into a caspase inhibitor, particularly an inhibitor of ICE, through additional steps known in the art.

DETAILED DESCRIPTION OF THE INVENTION

The following abbreviations are used throughout this application:

According to one embodiment, the invention provides a process for converting compound G to compound H:

wherein:

$R_1$ is a C2–C4 straight chain alkly optionally substituted at any carbon with one or more substituents selected from C1–C6 straight or branched alkyl, C2–C6 straight or branched alkenyl or alkynyl, O—C1–C6 straight or branched alkyl, O—C2–C6 straight or branched alkenyl or alkynyl, oxo, halo, $NO_2$, $N(R_4)(R_4)$, CN, Ar or O—Ar;

$R_2$ is selected from hydrogen, C1–$C_6$ straight or branched alkyl, C2–C6 straight or branched alkenyl or alkynyl or Ar, wherein said alkyl, alkenyl or alkynyl is optionally substituted with Ar;

n is 0 or 1;

Ar is a saturated, partially saturated or unsaturated monocyclic or bicyclic ring structure, wherein each ring contains 5 to 7 ring atoms and each ring optionally contains from 1 to 3 heteroatoms selected from O, N and S;

wherein Ar is optionally substituted at one or more ring atoms with one or more substituents independently selected from C1–C6 straight or branched alkyl, C2–C6 straight or branched alkenyl or alkynyl, O—C1–C6 straight or branched alkyl, O—C2–C6 straight or branched alkenyl or alkynyl, oxo, halo, $NO_2$, $N(R_4)(R_4)$, CN, $Ar_1$, O—$Ar_1$; wherein $Ar_1$ is a saturated, partially saturated or unsaturated monocyclic or bicyclic ring structure, wherein each ring contains 5 to 7 ring atoms and each ring optionally contains from 1 to 3 heteroatoms selected from O, N and S; and each $R_4$ is independently selected from H or an amino protecting group, with the proviso that both $R_4$ are not simultaneously hydrogen.

The term "amino protecting group", as used herein, means a moiety that prevents chemical reactions from occurring on the nitrogen atom to which that protecting group is attached. An amino protecting group must also be removable by a chemical reaction.

In one preferred embodiment, $R_1$ is substituted at the terminal carbon bound to the —COOH moiety with a protected amine. The term "protected amine" as used herein, means a nitrogen-containing moiety which can be chemically modified to an amine.

In another preferred embodiment, $R_1$ is substituted at the other terminal carbon (i.e., the one bound to the ring nitrogen) with oxo, making $R_1$ an acyl-containing moiety. More preferred is when $R_1$ contains both the protected amine substituent and the oxo substituent. One of the most preferred $R_1$ groups is:

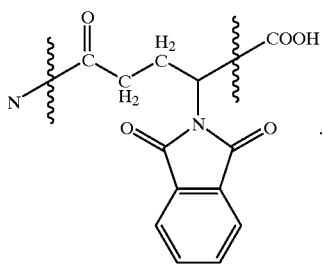

In another preferred embodiment, n is 1.

In yet another preferred embodiment, $R_2$ is t-butyl.

The method of this invention comprises the steps of:

(a) dissolving compound G in an organic solvent selected from dichloroethane, dichloromethane, toluene, chlorobenzene, chloroform or $CCl_4$;

(b) adjusting the temperature of the resulting solution to between 20° C. and 100° C.; and (c) adding more than about 2 equivalents of $SOCl_2$ and less than about 0.2 equivalents of N,N-Dimethylformamide to said solution over a period of between 2 and 18 hours.

Not all organic solvents may be used to dissolve compound G in step (a). The list of solvents set forth above are known to work. Other similar organic solvents may also work in the reaction and are to be considered part of the present invention. Preferably, the organic solvent is toluene.

Step (b) is preferably carried out at about 70° C. In step (c), it is preferred to use about 2 equivalents of $SOCl_2$ and about 0.1 equivalent of N,N-Dimethylformamide ("DMF"). It is also preferred that those two reagents be added slowly over a period of about 2 hours. Addition of the $SOCl_2$ and DMF over less than 2 hours tends to drastically reduce the efficiency of the reaction.

According to a preferred embodiment, excess equivalents of a base are added prior to step (b). In one preferred embodiment, about 5 equivalents of base are added to the reaction. Preferably, the base is selected from pyridine, collidine, lutidine, $NaHCO_3$, imidazole, triethylamine, N-methylmorpholine, diisopropylethylamine or $K_2CO_3$. Most preferably, the base is 2,6-lutidine.

Once the $SOCl_2$ and DMF have been added, the reaction is complete. At that point we prefer to purify compound H by diluting the reaction with the organic solvent used to dissolve compound G and then washing the solution first with $NaHCO_3$ and then with brine. The solution is then dried over $Na_2SO_4$ and concentrated.

Starting compound G may be obtained through standard synthetic routes well-known in the art. One such route is depicted below. Scheme 1 depicts the creation of intermediate E.

Scheme 1

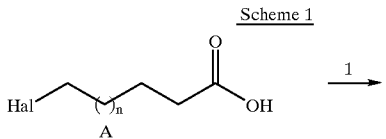

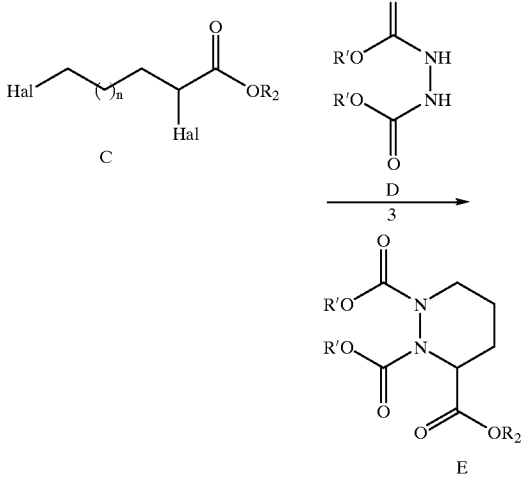

In Scheme 1, "Hal" is any halogen; each R' is an independently selected carboxyl protecting group; and n and $R_2$ are as defined above. Each of these steps is well-known in the art. Specifics concerning the conditions and reagents used at each step are set forth in the Examples.

The conversion of intermediate E to compound G is set forth in Scheme 2, below. That conversion may be achieved in one of two ways in the Scheme 2, depending upon the nature of $R_1$.

Scheme 2

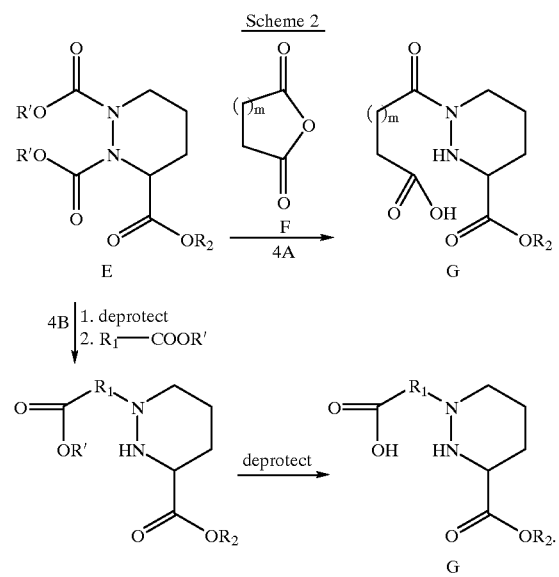

In Scheme 2, m is 0, 1 or 2; and R', $R_1$ and $R_2$ are as defined above. Also, in compound F any of the unsubstituted ring carbon atoms may be optionally substituted by one or more substituents independently selected from C1–C6 straight or branched alkyl, C2–C6 straight or branched alkenyl or alkynyl, O—C1–C6 straight or branched alkyl, O—C2–C6 straight or branched alkenyl or alkynyl, oxo, $NO_2$, $N(R_4)$ ($R_4$), CN, Ar, or O—Ar, wherein said alkyl, alkenyl or alkynyl is optionally substituted with Ar, and wherein $R_4$ and Ar are as defined above.

Reaction 4A comprises simultaneous deprotection and acylation if the carboxyl protecting groups can be removed by hydrogenolysis, e.g., if the protecting group is benzyl. If not, a deprotection step must precede the addition of the anhydride for the acylation reaction.

When compound F contains substituents and is not symmetrical, reaction 4A produces mixtures of compounds, wherein acylation of the N(2) nitrogen may occur at either C(O) functionality. This may be avoided by using substituents that favor the formation of the desired product. For example, in reaction 4A, the use of:

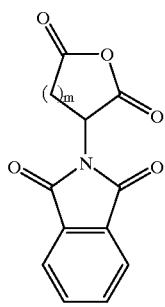

as compound F forces the formation of a compound wherein acylation of the N(2) nitrogen occurs at the C(O) functionality furthest away from the pthalimide substituent.

In order to avoid an unwanted reaction at the N(2) nitrogen in step 4B, the two carboxy protecting groups (R') on compound E should be different, such that the N(1) protecting group (—COOR') can be selectively removed without removing the N(2) protecting group.

Intermediate compound G containing the protected amine on $R_1$, and its subsequent conversion to compound H, may serve as the key intermediate and synthesis step, respectively, in an improvement in the synthesis of known caspase inhibitors, particularly inhibitors of interleukin-1 converting enzyme ("ICE"), such as those described in U.S. Pat. Nos. 5,716,929, 5,656,627, and 5,756,466 and in PCT publications WO 95/35308 and WO 97/22619.

Those inhibitors have the general formula (I):

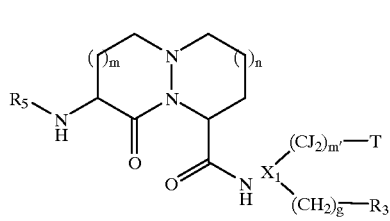

(I)

wherein:
any ring is optionally substituted at any carbon by $Q_1$, at any nitrogen by $R_5$, and at any atom by =O, —OH, —COOH, or halogen;
$X_1$ is CH or N;
g is 0 or 1;
m and m' are independently 0, 1 or 2;
n is 0 or 1;
each J is independently selected from —H, —OH, or —F, provided that when a first and a second J are bound to a C, and said first J is —OH, then said second J is —H;

T is —$Ar_3$, —OH, —$CF_3$, —C(O)—C(O)—OH, —C(O)—OH or any biosteric replacement for —C(O)—OH;

$R_3$ is —CN, —CH=CH—$R_9$, CH=N—O—$R_9$, —$(CH_2)_{1-3}$—$T_1$—$R_9$, —$CJ_2$—$R_9$, —C(O)—$R_{13}$, or —C(O)—C(O)—N($R_5$)($R_{10}$);

$T_1$ is —CH=CH—, —O—, —S—, —SO—, —$SO_2$—, —$NR_{10}$—, —$NR_{10}$—C(O)—, —C(O)—, —O—C(O)—, —C(O)—O—, —C(O)—$NR_{10}$—, O—C(O)—$NR_{10}$—, —$NR_{10}$—C(O)—O—, —$NR_{10}$—C(O)—$NR_{10}$—, —$S(O)_2$—$NR_{10}$—, —$NR_{10}$—$S(O)_2$— or —$NR_{10}$—$S(O)_2$—$NR_{10}$—;

each $R_5$ is independently selected from —H, —$Ar_1$, —C(O)—$Ar_1$, —$S(O)_2$—$Ar_1$, —$R_9$, —C(O)—$NH_2$, —$S(O)_2$—$NH_2$, —C(O)—$R_9$, —C(O)—O—$R_9$, —$S(O)_2$—$R_9$, —C(O)—N($R_{10}$)($Ar_1$), —$S(O)_2$—N($R_{10}$)($Ar_1$), —C(O)—N($R_{10}$)($R_9$), or —$S(O)_2$—N($R_{10}$)($R_9$);

each $R_9$ is a $C_{1-6}$ straight or branched alkyl group optionally singly or multiply substituted with —OH, —F, =O or $Ar_1$, wherein any $R_9$ may be substituted with a maximum of two $Ar_1$;

each $R_{10}$ is independently selected from —H or $C_{1-6}$ straight or branched alkyl;

$R_{13}$ is —H, —$Ar_1$, —$R_9$, —$T_1$—$R_9$ or —$(CH_2)_{1-3}$—$T_1$—$R_9$;

each $Ar_1$ is a cyclic group independently selected from a monocyclic, bicyclic or tricyclic aryl group containing 6, 10, 12 or 14 carbon atoms; a monocyclic, bicyclic or tricyclic cycloalkyl group containing between 3 and 15 carbon atoms, said cycloalkyl group being optionally benzofused; or a monocyclic, bicyclic or tricyclic heterocycle group containing between 5 and 15 ring atoms and at least one heteroatom group selected from —O—, —S—, —SO—, —$SO_2$—, =N—, or —NH—, wherein said heterocycle group optionally contains one or more double bonds and optionally comprises one or more aromatic rings;

$Ar_3$ is a cyclic group selected from phenyl, a 5-membered heteroaromatic ring or a 6-membered heteroaromatic ring, wherein said heteroaromatic rings comprise from 1–3 heteroatom groups selected from —O—, —S—, —SO—, —$SO_2$—, =N—, or —NH—;

wherein each $Ar_1$ or $Ar_3$ is optionally singly or multiply substituted at any ring atom by —$NH_2$, —C(O)—OH, —Cl, —F, —Br, —I, —$NO_2$, —CN, =O, —OH, -perfluoro $C_{1-3}$ alkyl,

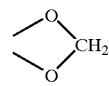

or —$Q_1$; and each $Q_1$ is independently selected from —$Ar_1$, —$R_9$, —$T_1$—$R_9$, or $(CH_2)_{1-3}$—$T_1$—$R_9$; provided that when —$Ar_1$ is substituted with a $Q_1$ which comprises one or more additional —$Ar_1$ groups, said additional —$Ar_1$ groups are not substituted with $Q_1$.

Preferably, the process of this invention is used as a step in the synthesis of a compound of formula I, wherein n is 1 and m is 2.

In another preferred embodiment, the process of this invention is used as a step in the synthesis of a compound of formula I, wherein $R_5$ is an acyl moiety selected from —C(O)—$Ar_1$, —C(O)—$NH_2$, —C(O)—$R_9$, —C(O)—O—$R_9$, —C(O)—N($R_{10}$)($Ar_1$), or —C(O)—N($R_{10}$)($R_9$).

In yet another preferred embodiment, the process of this invention is used as a step in the synthesis of a compound of formula I, wherein $X_1$ is CH; each J is H; m' is 1; T is —COOH or a biosteric replacement for —COOH; g is 0; and $R_3$ is —C(O)—$R_{13}$.

In the most preferred embodiment of using the process of this invention as a step in the synthesis of a compound of formula I, said compound has the structure:

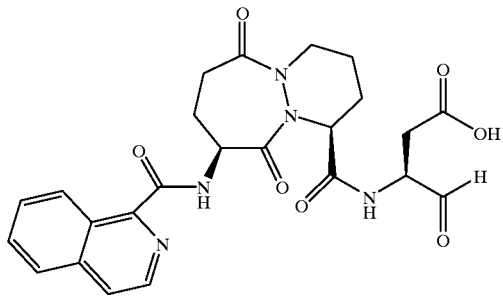

Alternatively, the process of this invention may be used as a step in the synthesis of a compound of the formula (II):

II

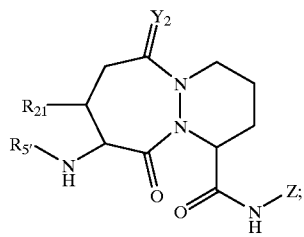

wherein:

Z is selected from

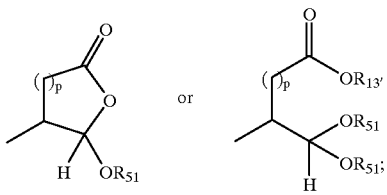

p is 1 or 2;

each $R_{5'}$ is independently selected from —C(O)—$R_{10'}$, —C(O)O—$R_{9'}$, —C(O)—N($R_{10'}$)($R_{10'}$), —S(O)$_2$—$R_{9'}$, —S(O)$_2$—NH—$R_{10'}$, —C(O)—CH$_2$—O—$R_{9'}$, —C(O)C(O)—$R_{10'}$, —$R_{9'}$, —H, —C(O)C(O)—O$R_{10'}$, or —C(O)C(O)—N($R_{9'}$)($R_{10'}$);

each $R_{9'}$ is independently selected from —$Ar_1$ or a —$C_{1-6}$ straight or branched alkyl group optionally substituted with $Ar_1$, wherein the —$C_{1-6}$ alkyl group is optionally unsaturated;

each $R_{10'}$ is independently selected from —H, —$Ar_1$, a —$C_{3-6}$ cycloalkyl group, or a —$C_{1-6}$ straight or branched alkyl group optionally substituted with $Ar_{3'}$, wherein the —$C_{1-6}$ alkyl group is optionally unsaturated;

$R_{13'}$ is selected from H, $Ar_1$, or a $C_{1-6}$ straight or branched alkyl group optionally substituted with $Ar_1$, —CONH$_2$, —O$R_{5'}$, —OH, —O$R_{9'}$, or —CO$_2$H;

each $R_{51}$ is independently selected from $R_{9'}$, —C(O)—$R_{9'}$, —C(O)—N(H)—$R_{9'}$, or two $R_{51}$ taken together form a saturated 4–8 member carbocyclic ring or heterocyclic ring containing —O—, —S—, or —NH—;

each $R_{21}$ is independently selected from —H or a —$C_{1-6}$ straight or branched alkyl group;

$Y_2$ is —H$_2$ or =O each $Ar_1$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, said heterocycle group optionally containing one or more double bonds, said heterocycle group optionally comprising one or more aromatic rings, and said cyclic group optionally being singly or multiply substituted by —Q$_1$;

each Q$_1$ is independently selected from the group consisting of —NH$_2$, —CO$_2$H, —Cl, —F, —Br, —I, —NO$_2$, —CN, =O, —OH, -perfluoro C$_{1-3}$ alkyl, $R_{5'}$, —O$R_{5'}$, —NH$R_{5'}$, O$R_{9'}$, —N($R_{9'}$)($R_{10'}$), $R_{9'}$, —C(O)—$R_{10'}$, and

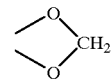

provided that when —$Ar_1$ is substituted with a Q$_1$ group which comprises one or more additional —$Ar_1$ groups, said additional —$Ar_1$ groups are not substituted with another —$Ar_1$.

Preferably, the process of this invention is used as a step in the synthesis of a compound of formula II, wherein $Y_2$ is O and $R_{21}$ is H.

In another preferred embodiment, the process of this invention is used as a step in the synthesis of a compound of formula II, wherein $R_{5'}$ is selected from —C(O)—$R_{10'}$, —C(O)O—$R_{9'}$, —C(O)—N($R_{10'}$)($R_{10'}$), —C(O)—CH$_2$—O—$R_{9'}$, —C(O)C(O)—$R_{10'}$, —C(O)C(O)—O$R_{10'}$, or —C(O)C(O)—N($R_{9'}$)($R_{10'}$).

In yet another preferred embodiment, the process of this invention is used as a step in the synthesis of a compound of formula II, wherein Z is

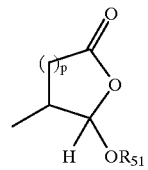

p is 1 and $R_{51}$ is selected from —$Ar_1$, —$C_{1-6}$ straight or branched alkyl or —$C_{1-6}$ straight or branched alkyl substituted with $Ar_1$.

In the most preferred embodiment of using the process of this invention as a step in the synthesis of a compound of formula II, said compound has the structure:

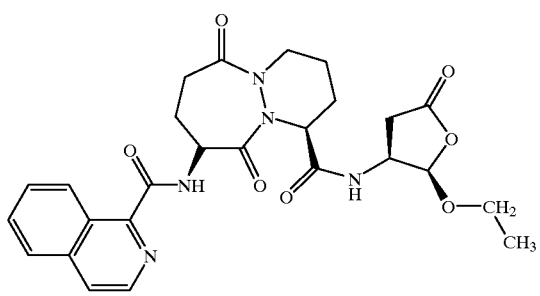

In the synthesis of these inhibitors, the terminal carbon of $R_1$ adjacent the —COOH moiety contains a protecting substituent. Preferably that protecting substituent is

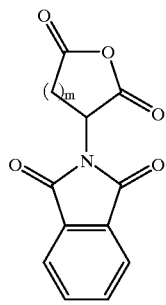

The synthesis steps from compound H to the inhibitors set forth above involve removal of the protecting substituent on $R_1$; coupling of the resulting amine to form the $R_5$—NH— or $R_{5'}$—NH— moiety in its place; hydrolysis of the $R_2$ group; and coupling of the amine

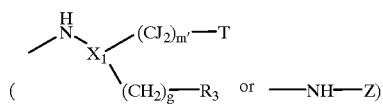

in its place;.

The removal of the protecting substituent on $R_1$ is typically carried out with hydrazine. The subsequent coupling of the $R_5$—NH— or $R_{5'}$—NH— moiety is achieved with standard coupling reagents, such as EDC, DCC or acid chloride.

Depending upon the nature of $R_2$, its hydrolysis may be achieved with an acid (when $R_2$ is t-butyl), a hydroxide (when $R_2$ is any other alkyl, alkenyl or alkynyl or Ar) or hydrogenolysis (when $R_2$ is an Ar-substituted alkyl, alkenyl or alkynyl). This produces the corresponding acid from the ester.

The acid is then coupled to the amine with standard coupling reagents, such as EDC, DCC or acid chloride.

In order that this invention be more fully understood, the following examples are set forth. These examples are for the purpose of illustration only and are not to be construed as limiting the scope of the invention in any way.

EXAMPLE 1

Synthesis of a 7,6 Scaffold for a Caspase Inhibitor

A.

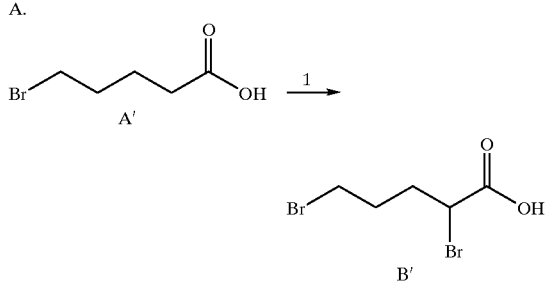

Compound A' was dissolved in 5 equivalents of $SOCl_2$ and then heated to 80° C. for 1 hour. The solution was then cooled to 50° C. and 2 equivalents of bromine were added. The solution was incubated at 50° C. for an additional 12 hours until the red color disappeared. We then cooled the solution to 10° C. and added 4 volumes of water. The solution was then re-heated to 50° C. for another hour. We then separated the organic and aqueous layer, washed the organic layer consecutively with water, $Na_2SO_3$ and then brine, removing the aqueous layer after each washing. The final organic layer was then isolated, dried over $Na_2SO_4$ and concentrated to produce compound B' as an amber oil.

B.

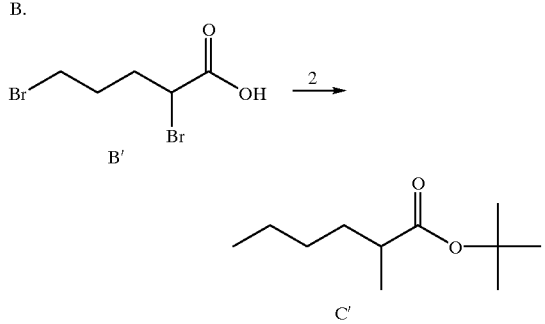

Compound B' was treated with 2 equivalents N,N-dimethyl formamide di-t-butyl acetal in a solution of toluene at ambient temperature. After 1 hour, the reaction was diluted with water and extracted with ethyl acetate. The organics were washed consecutively with $NaHCO_3$ and brine, dried over $Na_2SO_4$ and concentrated to afford compound C' as a yellow oil.

C.

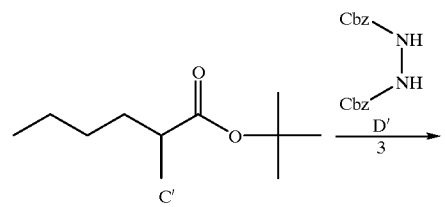

-continued

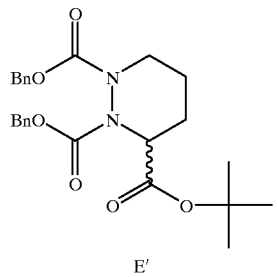

E'

Compound D' was dissolved in DMF and cooled in an ice-water bath. A solution of 2.5 equivalents potassium t-butoxide in THF was then added, followed by a solution of compound C' in DMF. The resulting mixture was stirred at ambient temperature for 16 hours. The reaction was then quenched by the addition of aqueous NH₄Cl and extracted 2 times with EtOAc. The organics were washed with water and brine, dried over Na₂SO₄ and concentrated to afford compound E' as an amber oil.

D.

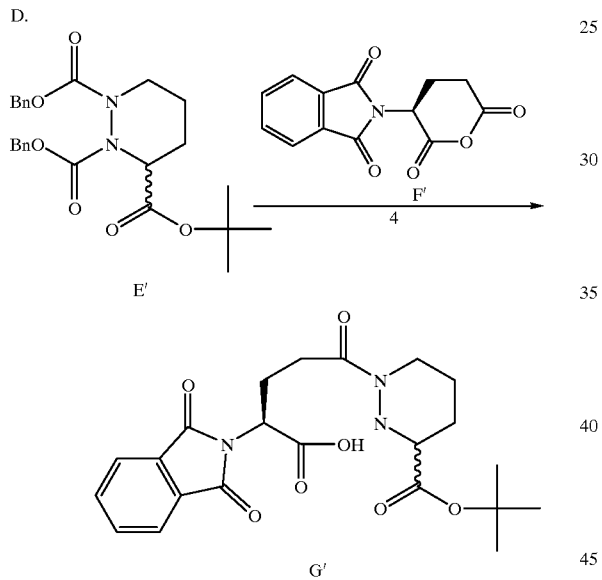

We dissolved compounds E' and F' together in THF. We then added a catalytic amount of 10% Pd/C and stirred the resulting suspension under a hydrogen atmosphere for 4 hours at ambient temperature. The catalyst was then filtered off and the filtrate concentrated to afford compound G' as a white foam/solid.

E.

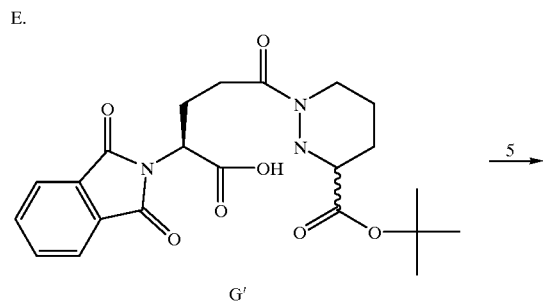

-continued

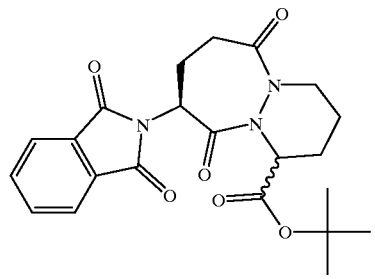

H'

We dissolved compound G in toluene and then added 5 equivalents of pyridine. The resulting solution heated to 70° C. A solution of 2 equivalents $SOCl_2$ and 0.1 equivalent of DMF in toluene was added slowly over 2 hours. The reaction was then diluted with toluene and washed consecutively with $NaHCO_3$ and brine. We then dried the organic layer over $Na_2SO_4$ and concentrated to afford compound H' as a yellow solid.

EXAMPLE 2

Use of Intermediate H' to Produce an Inhibitor of ICE

A.

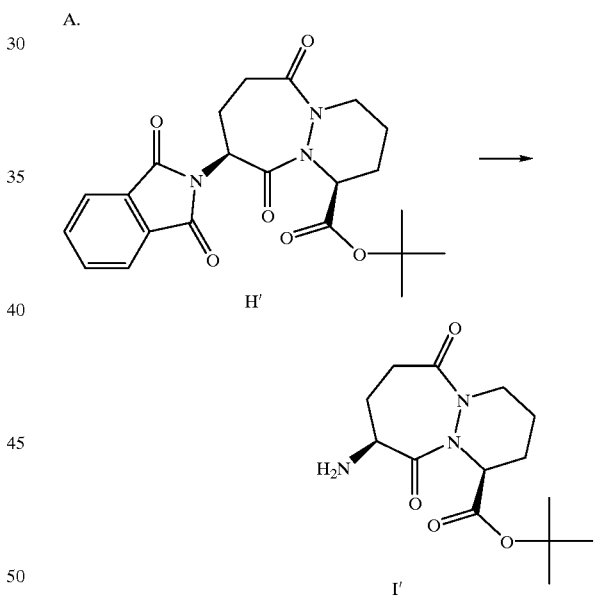

t-Butyl-9-amino-6, 10-dioxo-1,2,3,4,7,8,9,10-octahydro-6-H-pyridazino[1,2-a][1,2]diazepine-1-carboxylate (GB 2,128,984)

To a suspension of H' (107 g, 0.25 mol) in ethanol (900 mL) was added hydrazine (27 mL, 0.55 mol) and the resulting mixture was allowed to stir at ambient temperature. After 4 hours, the reaction was concentrated in vacuo and the resulting white solid was suspended in acetic acid (1 L of 2N) and allowed to stir at ambient temperature for 16 hours. The resulting white solid was filtered off and washed with water. The filtrate was made basic by the addition of solid sodium carbonate and the product extracted with dichloromethane. The organic layer was washed with brine, dried over magnesium sulfate and concentrated in vacuo to afford 79 mg of compound I' as a yellow viscous oil.

B.

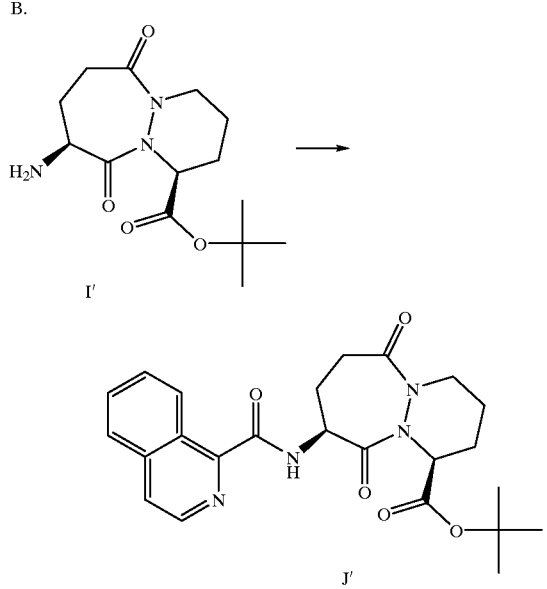

t-Butyl-9-(isoguinolin-1-oylamino)-6,10-dioxo-1,2,3,4,7,8,9,10-octahydro-6-H-pyridazino[1,2-a][1,2]diazepine-1-carboxylate To a solution of the amine I' (79 g, 0.265 mol) and isoquinolin-1-carboxylic acid (56 g, 0.32 mol) in dichloromethane:DMF (400 mL:400 mL) was added hydroxybenzotriazole (54 g, 0.4 mol) and 1-(3-dimethylaminopropyl)-3-ethylcarbodiimide hydrochloride (74 g, 0.39 mol) and the resulting mixture was allowed to stir at ambient temperature for 16 hours. The reaction mixture was poured into water and extracted with ethyl acetate. The ethyl acetate layer was washed with 0.5N sodium bisulfate, water, sodium bicarbonate, brine, dried over sodium sulfate and concentrated in vacuo to afford 122 g of compound J' as an orange solid-foam.

C.

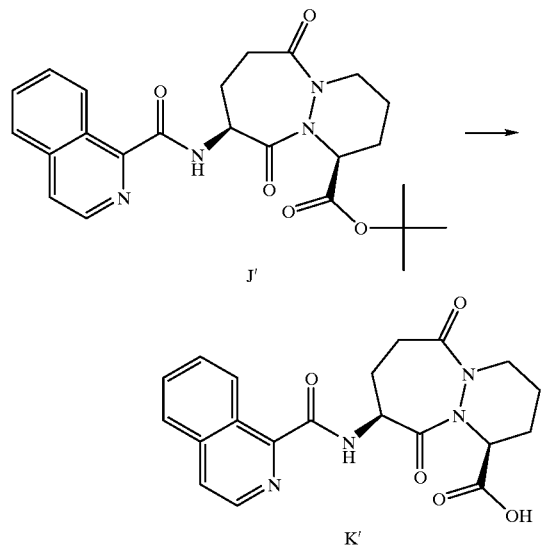

9-(isoquinolin-1-oylamino)-6,10-dioxo-1,2,3,4,7,8,9,10-octahydro-6-H-pyridazino[1,2-a][1,2]diazepine-1-carboxylic acid A solution of the ester J' (122 g) in dichloromethane and trifluoroacetic acid (200 mL) was allowed to stir at ambient temperature for 16 hours. The reaction mixture was concentrated to a black oil which was then triturated with acetonitrile and ether to afford 98 g of compound K' as a pale yellow solid.

D.

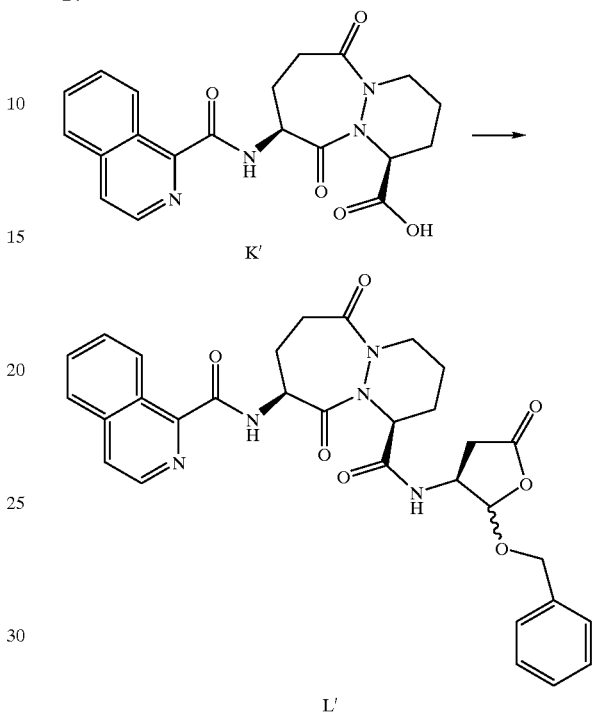

[1S, 9S (2RS, 3S)]N-(2-benzyloxy-5-oxotetrahydrofuran-3-yl)-6,10-dioxo-9-(isoquinolin-1-oylamino)-1,2,3,4,7,8,9,10-octahydro-6-H-pyridazino[1,2-a][1,2]diazepine-1-carboxamide To a solution of (3S, 2RS) 3-allyloxycarbonylamino-2-(benzyl)oxy-5-oxotetrahydrofuran [*Bioorg. & Med. Chem. Lett.*, 2, pp. 615–618 (1992)] (4.4 g, 15.1 mmol) in dichloromethane was added N,N-dimethylbarbituric acid (5.9 g, 3.8 mmol) then tetrakispalladium(0) triphenyl phosphine (1.7 g, 1.5 mmol) and the resulting mixture was allowed to stir at ambient temperature for 15 minutes. To the resulting mixture was added the acid, compound K' (5.0 g, 12.6 mmol), hydroxybenzotriazole (2.0 g, 14.8 mmol) then and 1-(3-dimethylaminopropyl)-3-ethylcarbodiimide hydrochloride (2.7 g, 14 mmol) and the reaction was allowed to stir for 3 hours at ambient temperature. The reaction mixture was then poured into water and extracted with ethyl acetate. The organics were washed with 0.5M sodium bisulfate, water, sodium bicarbonate, brine, dried over magnesium sulfate and concentrated in vacuo to afford 2.6 g of the crude product as a yellow foam. The crude material was purified by column chromatography (SiO$_2$, dichloromethane:acetone 9:1–3:1) to afford 1.2 g of the compound L'.

Compound L' and related compounds that may be synthesized using the method of this invention as an intermediate step are described in WO 97/22619, the disclosure of which is herein incorporated by reference. Those related compounds may be synthesized from the product of the method of this invention, H or H', through modifications of the procedure set forth in Example 2. Such modifications are well known in the art.

While we have hereinbefore presented a number of embodiments of this invention, it is apparent that my basic construction can be altered to provide other embodiments which utilize the methods of this invention. Therefore, it will be appreciated that the scope of this invention is to be defined by the claims appended hereto rather than the specific embodiments which have been presented hereinbefore by way of example.

We claim:
1. A process for producing a compound of the formula H:

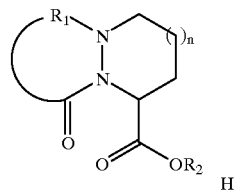

from a compound of the formula A:

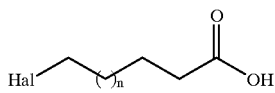

comprising the steps of:

(a) halogenating compound A to produce compound B:

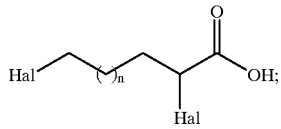

(b) esterifying the carboxylic acid moiety on compound B to produce compound C:

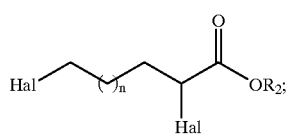

(c) reacting compound C with compound D:

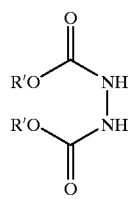

to produce compound E:

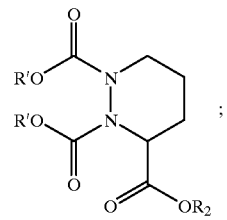

(d) reacting compound E with compound F:

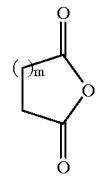

to produce compound G:

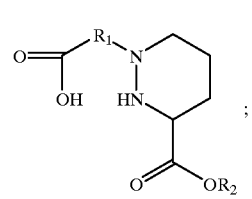

(e) dissolving compound G in an organic solvent selected from dichloroethane, dichloromethane, toluene, chlorobenzene, chloroform or CCl$_4$;
(f) adjusting the temperature of the resulting solution to between 20° C. and 100° C.; and
(g) adding more than about 2 equivalents of SOCl$_2$ and less than about 0.2 equivalents of N,N-Dimethylformamide to said solution over a period of between 2 and 18 hours; wherein:
$R_1$ is a C2–C4 straight chain alkyl optionally substituted at any carbon with one or more substituents selected from C1–C6 straight or branched alkyl, C2–C6 straight or branched alkenyl or alkynyl, O—C1–C6 straight or branched alkyl, O—C2–C6 straight or branched alkenyl or alkynyl, oxo, halo, NO$_2$, N(R$_4$)(R$_4$), CN, Ar or O—Ar;
$R_2$ is selected from C1–C6 straight or branched alkyl, C2–C6 straight or branched alkenyl or alkynyl or Ar, wherein said alkyl, alkenyl or alkynyl is optionally substituted with Ar;
n is 0 or 1;
Ar is a saturated, partially saturated or unsaturated monocyclic or bicyclic ring structure, wherein each ring contains 5 to 7 ring atoms and each ring optionally contains from 1 to 3 heteroatoms selected from O, N and S;
wherein Ar is optionally substituted at one or more ring atoms with one or more substituents independently selected from C1–C6 straight or branched alkyl, C2–C6 straight or branched alkenyl or alkynyl, O—C1–C6 straight or branched alkyl, O—C2–C6 straight or branched alkenyl or alkynyl, oxo, halo, NO$_2$, N(R$_4$)(R$_4$), CN, Ar$_1$, O—Ar$_1$; wherein Ar$_1$ is a saturated, partially saturated or unsaturated monocyclic or bicyclic ring structure, wherein each ring contains 5 to 7 ring atoms and each ring optionally contains from 1 to 3 heteroatoms selected from O, N and S;

each R$_4$ is independently selected from H or an amino protecting group, with the proviso that both R$_4$ are not simultaneously hydrogen;

each R' is a carboxy protecting, either the same or different; and each "Hal" is a halogen, either the same or different.

2. The process according to claim 1, wherein R$_1$ is substituted at the terminal carbon bound to the COOH moiety with a nitrogen-containing moiety which can be chemically modified to an amine.

3. The process according to claim 2, wherein R$_1$ is:

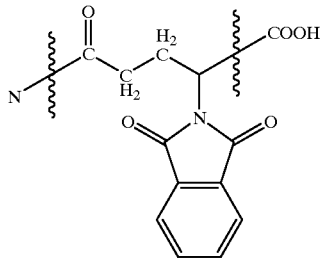

4. The process according to claim 1, wherein n is 1.
5. The process according to claim 1, wherein R$_2$ is t-butyl.
6. The process according to claim 5, wherein compound G has the formula:

G'

7. The process according to claim 1, wherein in step (e) of claim 1 the organic solvent is toluene.

8. The process according to claim 1, wherein step (f) of claim 1 is carried out at about 70° C.

9. The process according to claim 1, wherein in step (g) of claim 1, about 2 equivalents of SOCl$_2$ and about 0.1 equivalent of N,N-Dimethylformamide are used; and wherein said SOCl$_2$ and said N,N-Dimethylformamide are added over a period of about 2 hours.

10. The process according to claim 1, wherein prior to step (b) in claim 1 or prior to step (f) of claim 2, excess equivalents of a base selected from pyridine, collidine, lutidine, NaHCO$_3$, imidazole, triethylamine, N-methylmorpholine, diisopropylethylamine or K$_2$CO$_3$ are added to the solution containing compound G.

11. The process according to claim 10, wherein said base is 2,6-lutidine of which about 5 equivalents are added.

* * * * *